United States Patent [19]

Ljungdahl et al.

[11] 4,385,117
[45] May 24, 1983

[54] **HIGH ETHANOL PRODUCING DERIVATIVES OF *THERMOANAEROBACTER ETHANOLICUS***

[75] Inventors: Lars G. Ljungdahl; Laura H. Carriera, both of Athens, Ga.

[73] Assignee: University of Georgia Research Foundation, Inc., Athens, Ga.

[21] Appl. No.: 317,702

[22] Filed: Nov. 2, 1981

Related U.S. Application Data

[63] Continuation-in-part of Ser. No. 292,063, Aug. 12, 1981, abandoned.

[51] Int. Cl.³ .................. C12N 1/20; C12N 15/00; C12P 7/06
[52] U.S. Cl. ................... 435/161; 435/172; 435/253; 435/801
[58] Field of Search ............... 435/161, 253, 801, 172

[56] References Cited

U.S. PATENT DOCUMENTS 4,278,766  7/1981  Srinivasan et al. ............... 435/172
4,292,406  9/1981  Ljungdahl et al. ............... 435/801
4,292,407  9/1981  Ljungdahl et al. ............... 435/161
4,332,899  6/1982  Cooney et al. .................... 435/172

OTHER PUBLICATIONS

Sebek et al. eds.; *Genetics of Industrial Microorganisms;* Sermonti, G., 'Mutation and Microbial Breeding', ©1979, pp. 10-14.

*Primary Examiner*—Raymond N. Jones
*Assistant Examiner*—Elizabeth J. Curtin
*Attorney, Agent, or Firm*—William C. Lee, III

[57] ABSTRACT

Derivatives of the newly discovered microorganism *Thermoanaerobacter ethanolicus* which under anaerobic and thermophilic conditions continuously ferment substrates such as starch, cellobiose, glucose, xylose and other sugars to produce recoverable amounts of ethanol solving the problem of fermentations yielding low concentrations of ethanol using the parent strain of the microorganism *Thermoanaerobacter ethanolicus* are disclosed. These new derivatives are ethanol tolerant up to 10% (v/v) ethanol during fermentation. The process includes the use of an aqueous fermentation medium, containing the substrate at a substrate concentration greater than 1% (w/v).

40 Claims, No Drawings

HIGH ETHANOL PRODUCING DERIVATIVES OF *THERMOANAEROBACTER ETHANOLICUS*

The Government has rights in this invention pursuant to Contract No. DE-AS09-79ER10499-A001 awarded by the U.S. Department of Energy.

This application is a continuation in part of an application entitled "High Ethanol Producing Derivatives of *Thermoanaerobacter Ethanolicus*," Ser. No. 292,063, filed Aug. 12, 1981, now abandoned.

BACKGROUND AND SUMMARY OF THE INVENTION

This invention relates to derivative strains of a newly discovered microorganism *Thermoanaerobacter ehtanolicus*, a thermophilic anaerobe. More specifically, this invention relates to producing ethanol using derivatives of the microorganism *Thermoanaerobacter ethanolicus*.

The microorganism *Thermoanaerobacter ethanolicus* has been described as an extreme thermophilic, non-spore-forming anaerobic bacterium which ferments a variety of carbohydrates to ethanol as the main product (Wiegel, J. and Ljungdahl, L. G., Arch. Microbiol. 128, 343–348, 1981). Relatively few thermophilic anaerobic bacteria, which ferment substrates such as starch, cellobiose, glucose, xylose, and other sugars to ethanol as the main product, have been reported. The microorganism *Thermoanaerobacter ethanolicus* is described in U.S. Pat. No. 4,292,407 which is incorporated herein by reference. A related patent is U.S. Pat. No. 4,292,406 which is incorporated herein by reference.

The present invention overcomes problems of fermentations yielding low concentrations of ethanol using the microorganism *Thermoanaerobacter ethanolicus*.

The present invention produces ethanol at a substrate concentration in a fermentation medium greater than 1% (w/v) using biologically pure cultures of derivatives of the microorganism *Thermoanaerobacter ethanolicus*. The present invention provides derivatives having the ability to ferment substrates such as starch, cellobiose, glucose, xylose and other sugars to ethanol under anaerobic and thermophilic conditions in an aqueous, nutrient medium obtaining ethanol concentrations high enough to make continuous fermentations possible. Specifically, substrate can be added to a fermentation medium and ethanol can be removed therefrom during the same continuous fermentation.

The derivative strains, produced both through induced mutagenesis and multiple selections for spontaneous mutations (described in Examples I, II, and III below) differ from the parent strain, strain JW200 of the microorganism *Thermoanaerobacter ethanolicus* (ATCC 31550), in that the production of ethanol continues at a high rate although the ethanol concentration in the fermentation medium is greater than 1% (w/v) and substrate concentrations in the fermentation medium are greater than 1% (w/v). The following derivative strains are representatives of a large number of derivative strains obtained from the parent strain, strain JW200 of the microorganism *Thermoanaerobacter ethanolicus* (ATCC 31550). These biologically pure cultures of the representative derivative strains, specifically, strain JW200L-Large of the microorganism *Thermoanaerobacter ethanolicus* (ATCC 31936) representative of ultraviolet light mutagenesis and pyruvate selection; strain JW200Fe(3) of the microorganism *Thermoanaerobacter ethanolicus* (ATCC 31937) representative of iron deprivation selection and low growth on pyruvate; and strain JW200L-Fe(7) of the microorganism *Thermoanaerobacter ethanolicus* (ATCC 31938) representative of ultraviolet light mutagenesis, iron deprivation and low growth on pyruvate, are ethanol tolerant up to 10% (v/v) ethanol in the fermentation medium. The foregoing representative derivative strains produce ethanol at ethanol concentrations in a fermentation medium greater than 1% (w/v) whereas the parent strain does not produce ethanol at ethanol concentrations in a fermentation medium greater than 1% (w/v). The parent strain, strain JW200 of the microorganism *Thermoanaerobacter ethanolicus* (ATCC 31550), tolerates ethanol concentrations of up to 10% (v/v) ethanol in the fermentation medium only if given time to grow in low concentrations first. The above referenced derivative strains do not show this characteristic of the parent strain, strain JW200 of the microorganism *Thermoanaerobacter ethanolicus* (ATCC 31550).

It is an object of the present invention to produce ethanol at substrate concentrations in a fermentation medium above 1% (w/v) using biologically pure cultures of derivatives of the microorganism *Thermoanaerobacter ethanolicus*.

It is a further object to continuously produce recoverable amounts of ethanol from substrates such as starch, cellobiose, glucose, xylose, and other sugars.

These and other objects, aspects and advantages of this invention will become apparent from a consideration of the accompanying specification and claims.

DESCRIPTION OF THE PREFERRED EMBODIMENTS

The parent strain, strain JW200 of the microorganism *Thermoanaerobacter ethanolicus* (ATCC 31550), described in U.S. Pat. No. 4,292,407 which is incorporated herein by reference, is an extreme thermophilic, non-spore-forming anaerobic bacterium which ferments a variety of substrates such as starch, cellobiose, glucose, xylose, and other sugars to ethanol, carbon dioxide, lactate, acetate and hydrogen gas. When growing in an aqueous nutrient medium containing 10 g per liter (1% w/v) or less of substrate the major products are ethanol and carbon dioxide. If higher substrate concentrations are used, there is a shift away from ethanol production to production of the other products.

Strain JW200 of the microorganism *Thermoanaerobacter ethanolicus* (ATCC 31550) under optimal conditions, produces 1.8 mol of ethanol per mol of glucose. For example, at a concentration of 10 g per liter of glucose, one approximately obtains 0.5% (w/v) ethanol. This level of ethanol is not easily removed by known means of distillation; therefore, derivatives of the parent strain, strain JW200 of the microorganism *Thermoanaerobacter ethanolicus* (ATCC 31550), altered to grow at high substrate concentrations to yield ethanol above 1% (w/v) are useful. The representative derivatives mentioned above, strain JW200L-Large of the microorganism *Thermoanarobacter ethanolicus* (ATCC 31936), strain JW200Fe(3) of the microorganism *Thermoanaerobacter ethanolicus* (ATCC 31937), and JW200L-Fe(7) of the microorganism *Thermoanaerobacter ethanolicus* (ATCC 31938), produce ethanol at levels in the fermentation medium greater than 1.5% (w/v).

The following are microorganisms, culture methods, fermentations, strain maintenance procedures, morphology and taxonomy of the derivatives, isolation of the parent strain, strain JW200 of the microorganism *Thermoanaerobacter ethanolicus*.

(a) Organisms. The organisms are cultures of the parent strain, strain JW200 of the microorganism *Thermoanaerobacter ethanolicus* (ATCC 31550), the parent strain, and its high-ethanol producing derivatives, specifically, strain JW200L-Large of the microorganism *Thermoanaerobacter ethanolicus* (ATCC 31936), strain of JW200Fe(3) of the microorganism *Thermoanaerobacter ethanolicus* (ATCC 31937), and strain JW200L-Fe(7) of the microorganism *Thermoanaerobacter ethanolicus* (ATTC 31938).

(b) Culture Methods. The foregoing strains are routinely grown or cultivated under anaerobic and thermophilic conditions, specifically 68° C. and pH between 5.7 to 8.6 in anaerobic tubes (Bellco Glass Co., Vineland, N.J. No. 2046-18142) in the aqueous nutrient medium described in U.S. Pat. No. 4,292,407 which is incorporated herein by reference (Arch. Microbiol. 128, 343-348, 1981 which is incorporated herein by reference), and which is known in the art. Extruded cracked corn was used at concentrations of 20% (w/v) as a rapid indicator of hydrolysis of starch by the derivative strains. When concentrations of substrates exceeded 5% (w/v) yeast extract in the aqueous nutrient medium was increased to 0.6% (w/v). All of the aforementioned derivative strains produce mainly ethanol and only small amounts of lactate and acetate as fermentation products. Additionally, all the aforementioned derivative strains produce ethanol at a substrate concentration in the fermentation medium greater than 1% (w/v). Routine growth includes but is not limited to the following substrates: soluble and insoluble starch, pectin, disaccharides such as cellobiose, sucrose, lactose, and maltose, monosaccharides such as glucose, fructose, mannose, galactose, xylose, and ribose, and glycerol and pyruvate wherein the substrates are fermented to ethanol in the aqueous nutrient medium.

(c) Fermentations. Fermentations of the aforementioned substrates using the derivative strains continuously produce recoverable amounts of ethanol. More specifically, substrate can be added to a fermentation using the derivative strains, and ethanol can be removed therefrom during the same continuous fermentation. Fermentations are conducted under anaerobic and thermophilic conditions or under anaerobic and extreme thermophilic conditions. Extreme thermophilic conditions are understood to mean that fermentations are at 70° C. or higher. Fermentations are conducted at a pH range of about 5.7 to 8.6 and at a temperature range between about 40° C. and 78° C. Thus a process for continuously producing recoverable amounts of ethanol such that a substrate can be added to a fermentation and the ethanol can be removed therefrom during a fermentation is provided. This process comprises subjecting the aqueous nutrient medium containing the substrate at a substrate concentration in the fermentation medium, greater than 1% (w/v), wherein the substrate includes but is not limited to the following substrates: soluble and insoluble starch, pectin, disaccharides such as cellobiose, sucrose, lactose, and maltose, monosaccharides such as glucose, fructose, mannose, galactose, xylose, and ribose, and glycerol and pyruvate, to the fermentation action of a derivative of strain JW200 of the microorganism *Thermoanaerobacter ethanolicus* (ATTC 31550) wherein the derivative is derived through both induced and spontaneous mutagenesis. The process includes recovering ethanol from the fermentation medium. Distillation means may be used to recover ethanol from the fermentation medium under anaerobic and thermophilic conditions, or an inert carrier gas such as nitrogen bubbled through the fermentation vessel may carry the ethanol from the fermentation medium into a condensation unit.

(d) Strain Maintenance Procedure. Stock cultures of all of the aforementioned strains were maintained for 1 to 2 months at room temperature, about 25° C., after growth at 68° C. in the aqueous nutrient medium supplemented with 20% (w/v) cracked corn or by adding an equal amount of sterile anaerobic glycerol to a growing culture and storing the mixture at −20° C. for at least 18 months.

(e) Morphology and Taxonomy of the Derivatives. All of the derivative strains exhibit the morphologic and taxonomic characteristics of the parent strain, strain JW200 of the microorganism *Thermoanaerobacter ethanolicus* (ATCC 31550) described in U.S. Pat. No. 4,292,407 which is incorporated herein by reference.

(f) Isolation of the Parent Strain, Strain JW200 of the microorganism *Thermoanaerobacter ethanolicus* (ATCC 31550). The parent strain, strain JW200 of the microorganism *Thermoanaerobacter ethanolicus* (ATCC 31550) can be isolated by the methods described in a U.S. Pat. No. 4,292,407 which is incorporated herein by reference (Arch. Microbiol. 128, 343-348, 1981 which is incorporated herein by reference) and which is known in the art. Samples of the parent strain, strain JW200 of the microorganism *Thermoanaerobacter ethanolicus* (ATCC 31550) can also be obtained from the American Type Culture Collection (ATCC), 12301 Parklawn Drive, Rockville, Md. 20852, U.S.A.

EXAMPLE I

Ultraviolet Light Mutagenesis

Strain JW200 of the microorganism *Thermoanaerobacter ethanolicus* (ATCC 31550), the parent strain, was grown in the aqueous nutrient medium with 1% (w/v) soluble corn starch to early log phase, then transferred to a 3 ml quartz cuvette pregassed with argon and rinsed with reducing solution. The cells were held under a bacteriostatic UV light source at 10 cm for times up to 3 minutes. Samples were withdrawn every 30 seconds and diluted and rolled out (a type of plating technique for anaerobic microorganisms known in the art) in 2% (w/v) agar containing 2% (w/v) soluble corn starch. Individual colonies were analyzed randomly since most produced alcohol. Strain JW200L of the microorganism *Thermoanaerobacter ethanolicus* was derived from a UV treatment of 60 seconds. It produced in excess of 80 mM ethanol at 2% (w/v) starch. This strain was further selected for spontaneous mutations by iron deprivation and low growth on pyruvate to give strain JW200L-Fe(7) of the microorganism *Thermoanaerobacter ethanolicus* (ATCC 31938). Strain JW200L-Large of the microorganism *Thermoanaerobacter ethanolicus* (ATCC 31936) was derived from strain JW200L of the microorganism *Thermoanaerobacter ethanolicus* and further selected for good growth on pyruvate.

EXAMPLE II

Iron Deprivation

Ferredoxins, which are iron containing proteins, have been reported to be involved in ethanol production in some thermophilic anaerobic bacteria; therefore, 0.1 ml of a culture of strain JW200 of the microorganism *Thermoanaerobacter ethanolicus* (ATCC 31550) was transferred to 1 ml of the aqueous nutrient medium supplemented with 1% (w/v) starch and containing no iron. The culture was incubated at 60° C. for 30 minutes. At that time 250 µg/ml $Fe_2SO_4$ was added and incubation was continued for three days. Growth after 3 days was low. These cells were diluted 1/100 into the aqueous nutrient containing 2% (w/v) starch grown at 68° C. and assayed for ethanol after 24 hours. Cells from the culture strain JW200Fe of the microorganism *Thermoanaerobacter ethanolicus*, derived as described above, from 2% (w/v) starch produced 80 mM ethanol and 4 mM acetate over 24 hours.

The production of ethanol by strain JW200 of the microorganism *Thermoanaerobacter ethanolicus* (ATCC 31550), by the strain JW200L (described in Example I) of the microorganism *Thermoanaerobacter ethanolicus* and by strain JW200Fe of the microorganism *Thermoanaerobacter ethanolicus* with increasing starch concentrations is given in Table I below.

TABLE 1

Ethanol production from starch at increasing concentrations by two derivatives of strain JW200 of the microorganism *Thermoanaerobacter ethanolicus* (ATCC 31550) and the parent strain, strain JW200 of the microorganism *Thermoanaerobacter ethanolicus* (ATCC 31550).

| | Strains of *Thermoanaerobacter ethanolicus* | | |
|---|---|---|---|
| STARCH g/l | JW200 (ATCC 31550) ETHANOL mM | JW200L ETHANOL mM | JW200Fe ETHANOL mM |
| 5 | 58 | 59 | 59 |
| 10 | 82 | 98 | 82 |
| 20 | 25 | 210 | 90 |
| 50 | 8 | 320 | 110 |
| 100 | 5 | 242 | 245 |
| 140 | 11 | 142 | 360 |

EXAMPLE III

Pyruvate Selection

Strain JW200L (derived as described in Example I) of the microorganism *Thermoanaerobacter ethanolicus*, strain JW200Fe (derived as described in Example II) of the microorganism *Thermoanaerobacter ethanolicus*, and strain JW200L-Fe (derived by treatment described in Example I followed by treatment described in Example II) of the microorganism *Thermoanaerobacter ethanolicus*, were grown in the aqueous nutrient medium with 2% (w/v) solid agar supplemented with 1% (w/v) pyruvate and both 0.05% (w/v) glucose and xylose. Large and small colonies of strain JW200L of the microorganism *Thermoanaerobacter ethanolicus*, of strain JW200Fe of the microorganism *Thermoanaerobacter ethanolicus*, and of strain JW200L-Fe of the microorganism *Thermoanaerobacter ethanolicus* were selected. Each colony was grown in the aqueous nutrient medium supplemented with both 1% (w/v) cellobiose and 1% (w/v) xylose. The best strains were then transferred to the aqueous nutrient medium with 20% (w/v) cracked corn to test for the ability to grow at high substrate concentrations. The best cultures were transferred to the aqueous nutrient medium with increasing concentrations of soluble corn starch. The ethanol production was measured after four days and is shown in Table II below for representative strains (derivative strains). Samples of these derivative strains, specifically strain JW200L-Large of the microorganism *Thermoanaerobacter ethanolicus* (ATCC 31936), strain JW200Fe(3) of the microorganism *Thermoanaerobacter ethanolicus* (ATCC 31937) and strain JW200L-Fe(7) of the microorganism *Thermoanaerobacter ethanolicus* (ATCC 31938), can be derived as described in Example I, II and III above or samples can be obtained from the American Type Culture Collection (ATCC), 12301 Parklawn Drive, Rockville, Md. 20852, U.S.A.

TABLE II

Ethanol production from starch for derivatives of strain JW200 of the microorganism *Thermoanaerobacter ethanolicus* (ATCC 31550).

| | Derivative Strains of *Thermoanaerobacter ethanolicus* | | |
|---|---|---|---|
| STARCH g/l | JW200Fe(3) (ATCC 31937) ETHANOL mM | JW200L-Large (ATCC 31936) ETHANOL mM | JW200L-Fe(7) (ATCC 31938) ETHANOL mM |
| 31 | 336 | 175 | 315 |
| 62 | 470 | 246 | 195 |
| 200 | 416 | 210 | 150 |
| 242 | 272 | 205 | 180 |

Strain JW200L-Large of the microorganism *Thermoanaerobacter ethanolicus* (ATCC 31936), strain JW200Fe(3) of the microorganism *Thermoanaerobacter ethanolicus* (ATCC 31937), and strain JW200L-Fe(7) of the microorganism *Thermoanaerobacter ethanolicus* (ATCC 31938) have been maintained without reversion for a period of over six months.

The foregoing examples illustrate specific embodiments within the scope of this invention and are not to be construed as limiting said scope. While the invention has been described herein with regard to certain specific embodiments, it is not so limited. It is to be understood that variations and modifications thereof may be made by those skilled in the art without departing from the scope of the invention.

What is claimed is:

1. A biologically pure culture of a derivative of the microorganism *Thermoanaerobacter ethanolicus* having the ability to continuously produce recoverable amounts of ethanol such that a substrate can be added to a fermentation and the ethanol can be removed therefrom during a fermentation under anaerobic and thermophilic conditions in an aqueous nutrient medium containing the substrate at a substrate concentration in the fermentation medium greater than 1% (w/v) wherein the substrate is selected from the group consisting of starch, pectin, glycerol, pyruvate, monosaccharides, and disaccharides.

2. The biologically pure culture of the derivative of claim 1 wherein the derivative is derived from strain JW200 of the microorganism *Thermoanaerobacter ethanolicus* having the characteristics of ATCC 31550.

3. The biologically pure culture of the derivative of claim 1 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

4. The biologically pure culture of the derivative of claim 1 wherein the derivative is derived through mutagenesis means and selected for ethanol production in substrate concentrations of 2% (w/v).

5. The biologically pure culture of the derivative of claim 4 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

6. The biologically pure culture of the derivative of claim 4 having the ability to produce ethanol at an ethanol concentration in the fermentation medium greater than 1.5% (w/v).

7. The biologically pure culture of the derivative of claim 6 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

8. The biologically pure culture of the derivative of claim 6 wherein the derivative is ethanol tolerant up to 10% (v/v) ethanol in the fermentation medium.

9. The biologically pure culture of the derivative of claim 8 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

10. The biologically pure culture of the derivative of claim 8 wherein the fermentation is conducted under extreme thermophilic conditions.

11. The biologically pure culture of the derivative of claim 10 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

12. The biologically pure culture of the derivative of claim 8 wherein the fermentation is conducted at a pH range of about 5.7 to 8.6.

13. The biologically pure culture of the derivative of claim 12 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

14. The biologically pure culture of the derivative of claim 12 wherein the fermentation is conducted at a temperature range between about 40° C. and 78° C.

15. The biologically pure culture of the derivative of claim 14 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

16. The biologically pure culture of the derivative of claim 14 wherein the monosaccharides are selected from the group consisting of glucose, fructose, mannose, galactose, xylose, and ribose.

17. The biologically pure culture of the derivative of claim 16 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

18. The biologically pure culture of the derivative of claim 14 wherein the disaccharides are selected from the group consisting of cellobiose, sucrose, lactose and maltose.

19. The biologically pure culture of the derivative of claim 18 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

20. A process for continuously producing recoverable amounts of ethanol such that a substrate can be added to a fermentation and the ethanol can be removed therefrom during a fermentation which comprises subjecting an aqueous nutrient medium containing the substrate at a substrate concentration in the fermentation medium greater than 1% (w/v) wherein the substrate is selected from the group consisting of starch, pectin, glycerol, pyruvate, monosaccharides, and disaccharides, under anaerobic and thermophilic conditions to the fermentation action of a derivative of the microorganism *Thermoanaerobacter ethanolicus*.

21. A process according to claim 20 wherein the derivative is derived from strain JW200 of the microorganism *Thermoanaerobacter ethanolicus* having the characteristics of ATCC 31550.

22. A process according to claim 20 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

23. A process according to claim 20 wherein the derivative is derived through mutagenesis means and selected for ethanol production in substrate concentrations of 2% (w/v).

24. A process according to claim 23 wherein the derivative is selected from the group consisting of strain JW200L-Large of the microorganism *Thermoana-*

*erobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

25. A process according to claim 23 wherein ethanol is produced at an ethanol concentration in the fermentation medium greater than 1.5% (w/v).

26. A process according to claim 25 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

27. A process according to claim 25 wherein the derivative is ethanol tolerant up to 10% (v/v) ethanol in the fermentation medium.

28. A process according to claim 27 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

29. A process according to claim 27 conducted under extreme thermophilic conditions.

30. A process according to claim 29 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

31. A process according to claim 27 conducted at a pH range of about 5.7 to 8.6.

32. A process according to claim 31 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter enthanolicus* having the characteristics of ATCC 31938.

33. A process according to claim 31 conducted at a temperature range between about 40° C. and 78° C.

34. A process according to claim 33 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

35. A process according to claim 33 wherein ethanol is recovered.

36. A process according to claim 35 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

37. A process according to claim 35 wherein the monosaccharides are selected from the group consisting of glucose, fructose, mannose, galactose, xylose, and ribose.

38. A process according to claim 35 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

39. A process according to claim 35 wherein the disaccharides are selected from the group consisting of cellobiose, sucrose, lactose and maltose.

40. A process according to claim 39 wherein the derivative is selected from the group consisting of strain JW200L-Large of the microorganism *Thermoanaerobacter ethanolicus* having the characteristics of ATCC 31936, strain JW200Fe(3) of the microorganism *Thermoanaerobacter ethanolicus* having the characteristics of ATCC 31937, and strain JW200L-Fe(7) of the microorganism *Thermoanaerobacter ethanolicus* having the characteristics of ATCC 31938.

* * * * *